United States Patent [19]

Chipman et al.

[11] Patent Number: 5,591,740
[45] Date of Patent: Jan. 7, 1997

[54] USE OF DEBROMOHYMENIALDISINE FOR TREATING OSTEOARTHRITIS

[75] Inventors: Stewart Chipman, Reading, Mass.; David J. Faulkner, La Jolla, Calif.

[73] Assignees: OsteoArthritis Sciences, Incorporated, Cambridge, Mass.; The Reagents of the University of California, Oakland, Calif.

[21] Appl. No.: 472,902

[22] Filed: Jun. 7, 1995

[51] Int. Cl.$^6$ .................................... A61K 31/55
[52] U.S. Cl. ............................................ 514/215
[58] Field of Search ............................. 514/215

[56] References Cited

FOREIGN PATENT DOCUMENTS

WO93/16703  2/1993  WIPO .

OTHER PUBLICATIONS

Kobayashi, J., et al., "α–Adrenoceptor Blocking Action of Hymenin, A Novel Marine Alkaloid," *Experientia*, 44:86–87 (1988).

Pettit, G. R., et al., "Antineoplastic Agents 168 Isolation and Structure of Axinhydantoin," *Can. J. Chem.*, 68:1621–1624 (1990).

Cimino, S., et al., "Isolation and X–Ray Crystal Struction of a Novel Bromo–Compound from Two Marine Sponges," *Tetrahedron Lett.*, 23(7):767–768 (1982).

Kitagawa, I., "Marine Natural Products. XII. On the Chemical Constituents of the Okinawan Marine Sponge *Hymeniacidon aldis*," *Chem. Pharm. Bull.*, 31(7):2321–2328 (1983).

*Primary Examiner*—Theodore J. Criares
*Attorney, Agent, or Firm*—Hamilton, Brook, Smith & Reynolds, P.C.

[57] ABSTRACT

Disclosed is a method of treating osteoarthritis. The method comprises administering a therapeutic amount of debromohymenialdisine to an individual or animal with osteoarthritis. Debromohymenialdisine is able to slow the joint deterioration and cartilage degradation associated with the disease.

12 Claims, 3 Drawing Sheets

USE OF DEBROMOHYMENIALDISINE FOR TREATING OSTEOARTHRITIS

BACKGROUND

Osteoarthritis or degenerative joint disease is a slowly progressive, irreversible, often monoarticular disease characterized by pain and loss of function (Mankin and Brandt, Pathogenesis of Osteoarthritis in "Textbook of Rheumatology", Kelly, et al., (eds.) 3rd edition, W. B. Saunders Co., Philadelphia, pp.14699–111471) and Dean, *Arth. Rheum.* 20 (*Suppl.* 2):2 (1991)). The underlying cause of the pain and debilitation is the cartilage degradation that occurs as a result of the disease. A typical end-stage clinical picture includes complete erosion of the weight-bearing articular cartilage, requiring total joint replacement.

The pro-inflammatory cytokine interleukin-1 (IL-1) plays a major role in the cartilage matrix destructive processes observed in osteoarthritis (Pelletier, et al., *Sem. Arth. Rheum.*, 20:12 (1991) and McDonnell, et al., *Arth. Rheum.*, 35:799 (1992)). IL-1 has been demonstrated to upregulate the synthesis and secretion of the matrix metalloproteinases stromelysin and interstitial collagenase in a dose dependent manner (Stephenson, et al., *Biochem. Biophys. Res. Comm.* 144:583 (1987) and Lefebvre, et al., *Biochem. Biophys. Res. Comm.*, 152:366 (1990). These matrix metalloproteinases are responsible for the damage to the proteoglycan and collagen II components of the cartilage matrix which occur in osteoarthritis (Dean, et al., *J. Clin Invest.*, 84:678 (1989), Mort, et al., *Matrix*, 13:95 (1993) and Buttle, et al., *Arth. Rheum.*, 12:1709 (1993).

Currently, there is no therapeutic approach available that will slow the clinical progression of osteoarthritis, although steroids and non-steroidal anti-inflammatory drugs are used to ameliorate the pain and inflammation associated with the disease. Consequently, there is a need for new therapeutics which slow the joint degeneration caused by osteoarthritis.

SUMMARY OF THE INVENTION

The present invention is based on the discovery that debromohymenialdisine and analogs thereof slow the progression of osteoarthritis. It has also been found that these compounds inhibit the interleukin-1 induced degradation of glycosaminoglycan and extracellular matrix by chondrocytes in culture and explants of articular cartilage. Based on these discoveries, a method of treating osteoarthritis is disclosed.

The method comprises administering to an individual or animal with osteoarthritis a composition comprising a therapeutically effective amount of a compound having the structure of Formula I:

wherein:

R1 and R2 are each independently selected from the group consisting of -H and a halogen; and X is selected from the group consisting of:

or physiologically active salts thereof.

The method disclosed herein can slow joint degeneration in individuals with osteoarthritis. As a result, the loss of mobility often suffered by individuals with osteoarthritis can also be slowed. Reduced joint degeneration also results in the individual suffering less pain as a result of the disease.

DETAILED DESCRIPTION OF THE INVENTION

Debromohymenialdisine has been found to be useful in the treatment of osteoarthritis. This compound is a natural product isolated from the marine sponge Hymeniacidon. (Kobayashi, et al., *Experientia.*, 44:86 (1988) and Pettit, et al. , *Can. J. Chem.*, 68:1621 (1990)). Both Z -(1) and E- (2) stereoisomers of debromohymenialdisine are known, and can be represented by the structural formulas:

-continued (2)

Analogues of debromohymenialdisine are also useful in the treatment of osteoarthritis. These compounds contain the pyrroloazepine ring system found in debromohymenialdisine. This ring system is shown in (3), along with a numbering system for the ring atoms:

(3)

Analogues of debromohymenialdisine also have a five membered, nitrogen-containing heterocyclic ring which is bonded to the four position of the pyrroloazepine ring system. Examples of analogues of debromohymenialdisine include hymenialdisine (4), hymenin (5) and axinohydantoin (6), which have also been isolated from Hymeniacidon and from the marine sponges Axinella and Stylotella and can be represented, as follows:

(4)

(5)

(6)

Compounds used in the method of the present invention include those having the structure shown in Formula II:

(II)

R1 and R2 are each independently chosen from the group consisting of -H and a halogen. Suitable halogens include chlorine, bromine and iodine.

X is CH-A or C=A, wherein A is a five-membered nitrogen-containing heterocyclic ring. Also included are physiologically active salts of the compound.

In one embodiment, X is selected from the group consisting of:

In a preferred embodiment X has the structure shown in Formula (IV):

(IV)

and bromine is the preferred halogen.

In a more preferred embodiment R2 is -H. It is most preferred that R1 and R2 are -H, i.e. the compound is Z-debromohymenialdisine.

The method of the present invention can be used to treat individuals, i.e.-humans, or animals wi4th osteoarthritis.

Animals which can be treated with the method include dogs, cats, guinea pigs, farm animals and the like.

A therapeutically effect amount of the compound is the quantity of compound which, after being administered to an individual with osteoarthritis, brings about an amelioration of the disease processes associated with osteoarthritis without causing unacceptable side-effects. "Ameliorating the disease processes associated with osteoarthritis" can include lowering the amount of active matrix metalloproteinase in the individual, e.g. by inhibiting a matrix metalloproteinase, by preventing transcription of a gene which encodes a matrix metalloproteinase, by preventing the synthesis and/or secretion of a matrix metalloproteinase or by preventing interleukin-1 upregulation of matrix metalloproteinase activity. Alternatively, it can also include slowing, arresting or reversing the degradation and loss of function typically observed in a joint afflicted with osteoarthritis.

The skilled artisan will be able to determine the amount of compound which is to be administered to a human or veterinary animal. The amount of compound that is administered to an individual will depend on a number of factors including the general health, size, age, and sex of the individual and the route of administration. It will also depend on the degree, location and severity of the individual's osteoarthritis. One of ordinary skill in the art will be able to determine the precise dosage according to these and other factors. Typically, between about 1 mg per day and about 1000 mg per day are administered to the individual. Preferably, between about 1 mg per day and about 100 mg per day are administered to the individual, more preferably between about 1 mg per day and about 30 mg per day.

The compound can also be administered intraarticularly (for example by injection) into a joint with cartilage degradation caused by osteoarthritis. Other modes of parenteral administration which can be used include systemic administration, such as by intramuscular, intravenous, subcutaneous, or intraperitoneal injection.

In a preferred embodiment, the compound can be administered orally, for example, in capsules, suspensions or tablets. Alternatively, the compound can be administered topically near the joint with cartilage degradation caused by osteoarthritis.

The compound can be administered to the individual in conjunction with an acceptable pharmaceutical carrier as part of a pharmaceutical composition for treating osteoarthritis. Suitable pharmaceutical carriers may contain inert ingredients which do not interact with the compound. Standard pharmaceutical formulation techniques may be employed such as those described in Remington's Pharmaceutical Sciences, Mack Publishing Company, Easton, Pa. Suitable pharmaceutical carriers for intraarticular and other parenteral administration include, for example, sterile water, physiological saline, bacteriostatic saline (saline containing about 0.9% mg/ml benzyl alcohol), phosphate-buffered saline, Hank's solution, Ringer's-lactate and the like. Methods for encapsulating compositions (such as in a coating of hard gelatin or cyclodextran) are known in the art (Baker, et al., "Controlled Release of Biological Active Agents", John Wiley and Sons, 1986). Suitable carriers for topical administration include commercially available inert gels, liquids supplemented with albumin, methyl cellulose or a collagen matrix. Typical of such formulation are ointments, creams and gels. Preferred carriers for topical administration are those which facilitate penetration of the skin by the compound.

The compound can also be administered as at least one physiologically acceptable salt, such as, the hydrochloride salt, the hydrobromide salt and acetic acid salt.

In another embodiment of the present invention the composition, in addition to the compound, additionally comprises another pharmacologically active agent. Osteoarthritis is characterized by pain in the afflicted joints. Consequently, it is also advantageous to administer the compound with an analgesic or other pain-killing medication. Suitable analgesics include acetyl salicylic acid, acetominophen, and the like.

Osteoarthritis is also characterized by inflammation in the afflicted joints. Consequently, it is also advantageous to administer the compound together with an anti-inflammatory agent such as a non-steroidal anti-inflammatory drug or steroid (e.g. tramcinolone, amcinodide, and the like). Osteoarthritis is also characterized by over-activity of matrix metalloproteinase enzymes. Consequently, it is also advantageous to co-administer the compound with a matrix metalloproteinase inhibitor.

The invention will now be further and specifically described by the following examples.

EXEMPLIFICATION

EXAMPLE 1

Isolation of Z- and E-Debromohymenialdisine Analogs

Debromohymenialdisine was isolated from 250 grams of hydrated Stylotella by successively extracting with 100% methanol (3×1 liter) at room temperature. The combined methanol extracts were concentrated to an aqueous base and partitioned between ethyl acetate. The aqueous phase was concentrated and applied to a C-18 reverse phase HPLC with a water methanol gradient (90:10 to 40:60) as eluent.

Using the chondrocyte matrix breakdown assay described in Example 2, fractions were identified which contained compounds capable of inhibiting interleukin-1 induced cartilage degradation. Preliminary structure determination showed that a class of pyrrole containing compounds were responsible for activity.

Z-Debromohymenialdisine, E-debromohymenialdisine, axinohydantoin and hymenialdisine were isolated from active fractions by further by applying to a C-18 reverse phase HPLC with water:methanol (ratio for the Z-isomer, the E-isomers, axinohydantoin and hymeniadlisine are 82:12, 72:28, 72:28 and 70:30, respectively) and plus the addition of 1% trifluoroacetic acid.

EXAMPLE 2

Inhibition of Cartilage Degradation By Z- and E-Debromohymenialdisine in a Chondrocyte Cell Culture Matrix Breakdown Assay Isolation of the Cartilage A cell culture assay was used to measure the ability of the test compounds to slow the degradation of the extracellular matrix by a metalloproteinase. This assay measured the amount $^{35}S$ released from chondrocytes grown in a media with $^{35}S$ labeled sodium sulfate. The cell culture assay was carried out as follows:

Two or three 1 to 3 week old calf joints were obtained from an abattoir. The proximal end of the shank was about 4–5" long to facilitate immobilization in the holder. The joint was kept cool and transported on ice. The exterior of the intact joints was washed well with a suitable anti-microbial soap, rinsed clean with warm water, rinsed in betadine and then finally rinsed with 70% ethanol. Up to this point all steps were done in a manner to ensure that the joint was kept as clean as possible. All subsequent steps were performed in a sterile field (i.e., in a Edgeguard laminar flow tissue culture hood). The joint was immobilized and the synovial fluid was aspirated with a needle and syringe. The joint was then cut open to expose the articular cartilage using a #21 scalpel. Using locking hemostats, forceps and a #15 scalpel, the cartilage was excised in full thickness pieces. Care was taken not to cut too deep into the subchondral bone to prevent bleeding. The cartilage pieces were placed into a 50 mL centrifuge tube containing 25 mL of Delbecco's phosphate buffered saline (D-PBS) supplemented with 1% antibiotic solution (penicillin, streptomycin and fungizone; GIBCO/BRL). The slices from each joint were then placed into separate 50 mL centrifuge tubes. The D-PBS was decanted and replaced with 25 mL of fresh D-PBS supplemented with antibiotics and subsequently agitated gently.

Enzymatic Digestion

The cartilage pieces were transferred to a fresh 50 mL centrifuge tube and rinsed once more with 25 mL of D-PBS minus antibiotics. An enzymatic digestion solution containing 1 mg/mL of hyaluronidase in serum-free 1:1 DMEM/Ham's F-12 (DMEM/F12) was prepared. This solution was filter sterilized with 0.22 mm Milex—GV filter and kept on ice until ready to use. The cartilage pieces were digested with approximately 5 mL of hyaluronidase solution per joint for 2×15 minutes at 37° C. in the 50 mL centrifuge tube with gentle agitation at the 15 minute mark. This procedure removed residual hyaluronic acid from the surface of the chips. The enzymatic digestion solution was then aspirated and the cartilage pieces were rinsed with 25 mL of D-PBS.

A second enzymatic digestion solution containing 2.5 mg trypsin and 2 mg collagenase P per mL serum-free DMEM/F12 was prepared. This solution was also filter sterilized with a 0.22 mm Millex—GV filter and kept on ice until ready to use. The cartilage pieces were digested with approximately 5 mL of trypsin: collagenase solution per joint for 2×15 minutes at 37° C. in the 50 mL centrifuge tube with gentle agitation at the 15 minute mark. This procedure removed the synovial fibroblasts and any adherent connective tissue from the surface of the chips. The enzymatic digestion solution was then carefully removed and saved and the cartilage pieces were rinsed with 25 mL of D-PBS.

A third enzymatic solution containing 2 mgs of collagenase P (BMB) per mL serum-free DMEM/F12 was prepared. This solution was filter sterilized with a 0.22 mm Millex—GV filter and kept on ice until ready to use. The pre-digested cartilage pieces were finally digested with approximately 20 mL of enzymatic digestion solution per joint for 5–6 hours at 37° C. in a Bellco stirring digestion flask, at which point the cartilage was fully digested away.

Culture and Growth of Isolated Chondrocytes

The enzymes in the synovial fibroblast and chondrocyte digest were neutralized by addition of an equal volume of DMEM/F12 supplemented with 5% fetal bovine serum. Fibroblasts were plated in DMEM at a cellular density of $6.6\times10^3$ cells per cm². The chondrocytes were recovered by filtration through a 70 mm nylon Cell Strainer (Falcon Labware, Inc.), which removed the remaining undigested tissue pieces and clumps of cells. Chondrocytes were then collected by centrifugation at 1000× g for 10 minutes at room temperature. The chondrocytes were then resuspended in 40 mL of DMEM/F12 supplemented with 5% fetal bovine serum. A 200 μL aliquot in 20 mL of isoton was quantitated in a Coulter counter. Chondrocytes were diluted with 1:1 (v/v) DMEM/F-12 supplemented with 5% fetal bovine serum to a density of $2\times10^4$ cells per cm² of culture surface. This density allowed the cells to be at confluence as soon as they are plated. Four days later the cells were again fed with media. This time period ensured the attachment of the chondrocytes to the plastic well.

Chondrocytes were plated at $8\times10^4$ cells/2 cm² per well with 0.5 mL of 1:1 (v/v) DMEM/F12 supplemented with 10% fetal bovine serum in 24 well plates and incubated for 4 days. The cultures were then fed on days 4, 7, 11, 14, 18 and 21 with 0.5 mL/well of DMEM/F12 plus 10% fetal bovine serum. At this time the cells were densely confluent and have developed a three-dimensional extracellular matrix.

Radiolabel & Chase of Chondrocytes

On day 22, the wells are rinsed 2×1 mL with D-PBS and incubated for 30 minutes in 0.5 mL of DMEM/F12 per well. This starve media was removed, replaced with 0.5 mL/well of DMEM/F23 plus 10 μCi $^{35}$S labeled sodium sulfate per well and incubated for 48 hours at 37° C. On day 24, the labeling media is removed. The wells were then re-fed with 0.5 mL of DMEM/F12 plus 10% fetal bovine serum. The cultures were "chased" with cold sulfate (in the tissue culture media) for two more days and on day 26 were re-fed with 0.5 mL of fresh DMEM/F12 plus 10% fetal bovine serum.

Experimental Addition and Harvest

On day 27, the wells were rinsed 2×1 mL with D-PBS and incubated for 22–24 hours with 0.5 mL/well of serum free DMEM/F12, 1 ng/ml of rhIL-1α, plus the compound being tested at the desired concentrations. The wells were carefully rinsed to remove any residual fetal bovine serum which could affect the final results. A first control was run in which the assay was carried out in the absence of the compound being tested. A second control was also run in which the assay was carried out in the absence of test compound and rhIL-1α. On day 28 the 0.5 mL of media was removed and counted in a mini-vial with 4 mL of scintillation fluid. The cell layer was rinsed 1×1 mL with D-PBS and harvested with 0.5 mL of 1× trypsin-EDTA (purchased from Gibco-BRC, Life Technologies, Gaithersburg, Md.) (incubated for at least 15–20 minutes) for scintillation counting as before. The data is expressed as percent radiolabel released in the media of the total according to the formula:

$$\% \text{ release} = \frac{cpm_{media}}{(cpm_{media}) + (cpm_{cell\ layer})}$$

The average percent release is used to determine a percent inhibition according to the following formula:

$$\% \text{ Inhibition} = \frac{A-B}{C-B} \times 100,$$

wherein,
A=% release in presence of test compound;
B=% release in control; and
C=% release in presence of rhIL-1α.

Z-debromohymenialdisine, E-debromohymenialdisine, hymenialdisine and axinohydantoin were tested in the chondrocyte matrix breakdown assay described above. The $IC_{50}$ value for each compound tested in the assay is given in the Table below. Z-debromohymenialdisine and E-

TABLE

Figure 1:
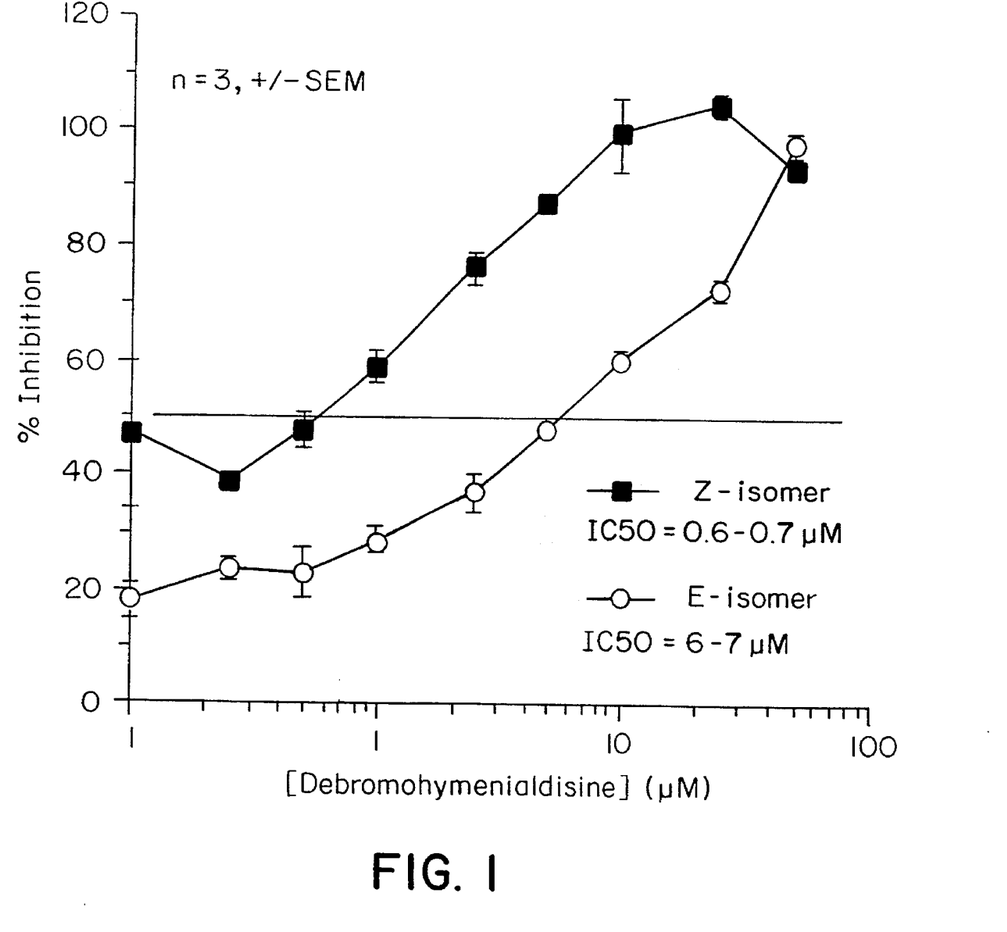
FIG. 1 is a graph illustrating the degree of inhibition of proteoglycan degradation by Z- and E-debromohymenialdisine in the chondrocyte matrix breakdown assay.

| Inhibition of Proteoglycan Degradation by Marine Alkaloids from Styllotella | |
|---|---|
| Compound | $IC_{50}$ |
| Z-debromohymemialdisine (1) | 0.8 µM |
| E-debromohymemialdisine | .6 µM |
| Axinohydantoin (3) | >50 µM |
| Hymenialdisine (2) | >50 µM | debromohymenialdisine both inhibited proteoglycan degradation. The Z- isomer was more active than the E-isomer with $IC_{50}$s of 0.8 and 6 µM, respectively. FIG. 1 show the inhibition of proteoglycan degradation by the Z-and E- isomer of debromohymenialdisine over a range of concentrations. The data are expressed as percent inhibition compared to control and interleukin-1 stimulated cultures versus inhibitor concentration. Each data point represents an average of four wells plus or minus the standard error of the mean. Both compounds exhibited a broad, shallow dose response curve.

Example 3

Inhibition of Cartilage Degradation in the Bovine Cartilage

Explant Assay by Z- and E-Debromohymenialdisine

A tissue culture assay was used to measure the ability of the compounds of the present invention to slow the degradation of the extracellular matrix by metalloproteinases. This assay measured the amount of $^{35}$S-glycosaminoglycan ($^{35}$S-GAG) released from labeled bovine cartilage explants.

Knee joints from a 1 to 3 week old calf were obtained immediately after sacrifice from the Abattoir and then transported on ice. The intact joints were washed well with tap water and soaked in 50% (v/v) Povidine iodine solution, obtained from Burre National, Inc., Baltimore, Md. All subsequent steps were performed in a laminar flow tissue culture hood using standard sterile technique. The joint was immobilized in a shank holder and the joint capsule was cut open to expose the articular cartilage. Cartilage explant plugs, approximately 15 mg wet weight, were removed from the flat articulating surfaces in the lower-most region of the knee joint using a sterile steel cork-borer and collected in a 250 mL roller bottle containing about 100 mL fresh Delbecco's minimum essential medium (DMEM), obtained from Gibco BRC, Life Technologies, Gaithersburg, Md., containing 4.5 g/l (D)-glucose and (L)-glutamine, without sodium pyruvate. The fresh media also contained enough Hepes buffer and sodium bicarbonate such that the pH was about 7.4. The media was then further supplemented just before use with 100 units Penicillin, 100 µg Streptomycin, and 50 µg (L)-ascorbic acid per mL of medium.

Once collected, the explant plugs were washed four times with 50 mL fresh DMEM. The plugs were then placed in the incubator for a minimum of 1 hour to equilibrate, before proceeding to make disks from the articulating surface of each plug. A 1 mm thick disk was sliced from individual plugs from the end that was the articulating surface of the joint. The plug was held steady in the sterile template (4 mm diameter ×1.5 mm deep) using sterile forceps. A scalpel blade was used to carefully slice off the disk. Only the superficial articulating surface responded well in culture.

Individual disks obtained were transferred to a tissue culture flask containing about 100 mL fresh media. The flask containing the disks was placed in an incubator at 37° C. (with 5% $CO_2$, 95% air) and allowed to equilibrate overnight and at least one additional day before labeling. When ready to label, the old media was replaced with 50 mL fresh media containing about 500 µCi $^{35}$S-Sodium Sulfate. The plugs were labeled in bulk for about 48 hours. The next morning, the "hot" media was removed and replaced with fresh "cold" media. The disks were again allowed to equilibrate overnight before being used for actual experiments.

The media in which the disks were stored was changed immediately prior to performing the assay. The disks were then returned to the incubator until the test media and the two control media had been prepared. The test media consisted of the desired concentration of a compound being tested for its ability to inhibit extracellular matrix degradation and concomitant recombinant human Interleukin rhIL-1α (5 ng/mL) in fresh DMEM solution. The control media were identical to the test media, except that the first control media lacked rhIL-1α and the second control media lacked the test compound. 250 µL of each of the test and control media were transferred to separate 96-well TC plates. Flamed forceps were used to transfer a disk from the incubator to each 96-well TC plates that had been filled with either the test media or one of the two control media.

The TC plates were then placed in the incubator and cultured for 3–4 days (initial incubation with rhIL-1α alpha takes at least 3 days to stimulate endogenous metalloproteinases). A 50 µL aliquot of media from each TC plate was saved and counted. The rest of the media was removed with a suction device.

The cartilage disks from each TC plate were also saved for counting. The disks were removed with forceps and placed in microcentrifuge tubes and then dissolved in 250 µL of full strength Formic Acid. The tubes were capped and placed at 65°–70° C. in a block-heater for 4–6 hours. A 50 µL aliquot was then counted.

The percent $^{35}$S-GAG release is calculated as follows:

$$\% \ ^{35}S\text{-}GAG \ release = \{(cpm_{medium})/(cpm_{medium} + cpm_{explant})\} \times 100\%$$

The percent inhibition at 50 µM of extracellular matrix damage in cartilage explant was calculated as follows:

$$\% \ \text{Inhibition} = \frac{(A-B)-(C-B)}{(A-B)} \times 100,$$

wherein
A=% GAG release induced by rhIL-1α;
B=% GAG release in the absence of rhIL-1α; and
C=% GAG release in the presence of rhIL-1α plus 50 µM of compound being tested.

Figure 2:
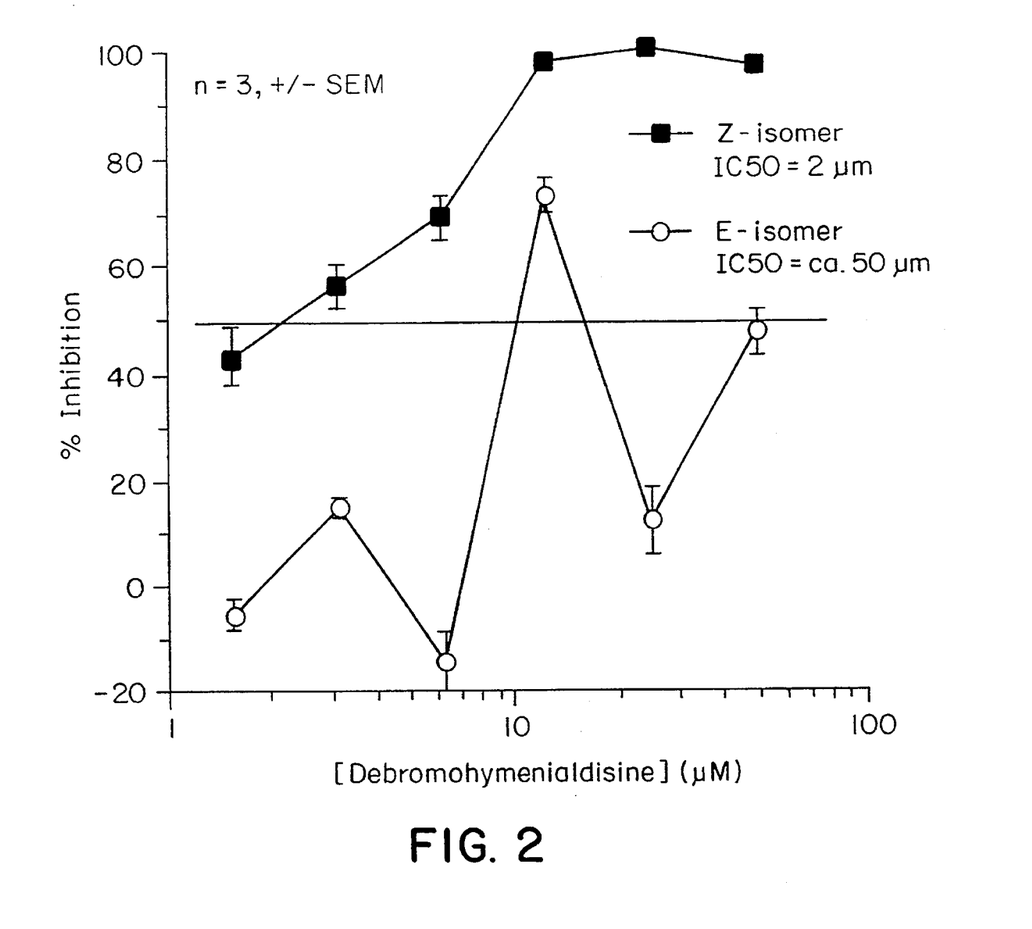
FIG. 2 is a graph illustrating the degree of inhibition of proteoglycan degradation by Z- and E-debromohymenialdisine in the bovine articular cartilage explant assay.

Both Z-debromohymenialdisine and E-debromohymenialdisine were tested in the bovine cartilage explant assay, as described above. Both the Z- and E-isomers inhibited interleukin-1 stimulated proteoglycan degradation with $IC_{50}$s of 2 µM and 50 µM, respectively. FIG. 2 shows the percent inhibition of these two compounds over a range of concentrations compared with control and interleukin-1 stimulated cultures versus inhibitor concentration. Each data point represents an average of four wells plus or minus the standard error of the mean. Both compounds exhibited a broad, shallow dose response curve in both assay systems.

EXAMPLE 4

Induction of Osteoarthritis in Guinea Pigs by Surgical

Induction of Joint Instability

Thirty five male Hartley guinea pigs 40 days old, were purchased from Charles River Laboratories. Each group consisted of 5 animals that were euthanized at 1, 2, 3, 4, 5, 6 and 8 months post-surgery. Ketamine 40 mg/kg, Xylazine 5 mg/kg and Fentanyl 0.1 mg/kg sc were used for anesthesia. Naloxone hydrochloride was given at 0.1 mg/kg following surgery. For radiography, animals were sedated with Xylazine 10 mg/kg sc and superficially anesthetized with Ketamine 20 mg/kg sc.

Surgery was performed under direct visualization using a dissecting microscope at 7.5 fold magnification. A medial longitudinal parapatellar incision was followed by division of the capsule and synovial layers. A partial medical menisectomy was followed by transection of the anterior cruciate ligament. Confirmation of the ligament transection was obtained by a positive anterior drawer sign. The capsule was continuously sutured with 5-0 VICRYL™ and the skin was closed with staples.

After the animals were sacrificed, joints were prepared for histological examination by standard techniques. Joints were fixed for 14 days in 10% formalin. Knees were then decalcified in 20% Formic acid in PBS, pH 7.2 for 24 hours. Sections cut at 5μ were stained with Safranin O, Fast Green and Hematoxylin. Radiographic evaluation was performed with antero-posterior and lateral views. A dental X-Ray unit and DF-50 film were used. Histopathological scoring was performed by two blinded, independent observers using the Mankin criteria (Mankin, H. J., "Biochemical and Metabolic Aspects of Osteoarthritis," *Orthopedic Clinics of North America*, 2:19–30 (1971). This evaluation system grades the structural defects, cellular changes, loss of proteoglycan as reflected by Safranin 0, and disruption of an antatomic landmark reflecting the transition to calcified cartilage. The Mankin scoring criteria are listed below:

| Mankin Scoring Criteria | |
| --- | --- |
| Structure | |
| Normal | 0 |
| Surface Irregularities | 1 |
| Pannus and Surface Irregularities | 2 |
| Clefts to the Transition Zone | 3 |
| Clefts to the Calcified Zone | 4 |
| Complete Disorganization | 5 |
| Cells | |
| Normal | 0 |
| Diffuse Hypercellularity | 1 |
| Cloning | 2 |
| Hypocellularity | 3 |
| Safranin O Straining | |
| Normal | 0 |
| Slight Reduction | 1 |
| Moderate Reduction | 2 |
| Severe Reduction | 3 |
| No dye noted | 4 |
| Tidemark Integrity | |
| Intact | 0 |
| Cross by Blood Vessels | 1 |

Lesions were initially localized to the weight bearing regions on the medial side of the tibia plateau and femoral condyle. The developing osteoarthritis was characterized by cartilage erosion and fibrillation. Radiographic examination revealed sclerosis, cysts and osteophytes. Osteophytes were first noted at three months post-surgery.

Figure 3:
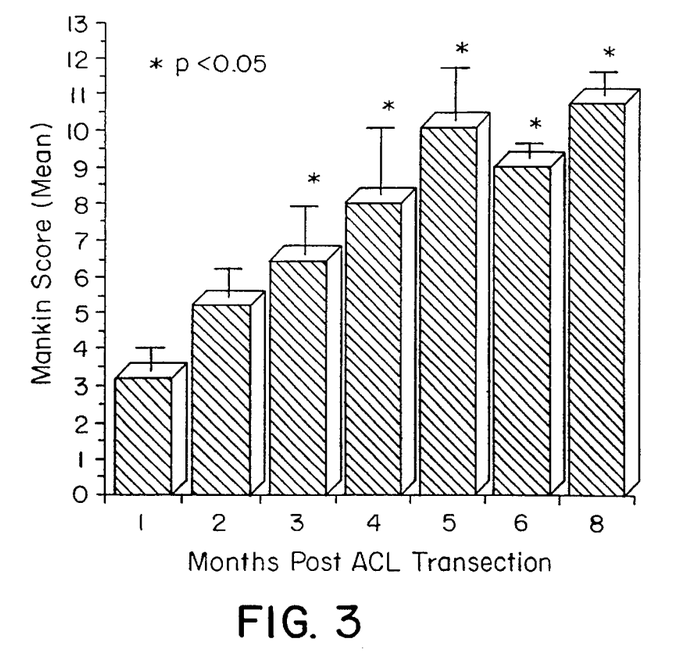
FIG. 3 is a graph illustrating the development of osteoarthritis over time in Hartley guinea pigs following transection of the anterior cruciate ligament.

The histopathological evaluation of the knee by the Mankin Criteria is depicted in the FIG. 3. The results indicate that there was disease progression starting from a Mean Mankin score of 3.2 (±1.3) at one month post-surgery to 10.7 (±0.7) at 8 months. Changes were statistically significant ($p<0.05$) when compared with the group at 1 month. Changes observed included cartilage hypertrophy, erosion and fibrillation, loss of proteoglycan, chondrocyte cloning and osteophytes. The Hartley guinea pig has been previously reported to have a high incidence of spontaneous osteoarthritic disease (Bendele, A. M. and Julman, J. F. "Spontaneous Cartilage Degeneration in Guinea Pigs," *Arthritis and Rheumatism*, 31:561–565 (1988). The surgical procedure presented here augments this propensity. The fidelity and anatomic location of the lesions presented and the progressive nature of the disease indicates that Hartley guinea pigs which have undergone the procedure described above are a valid model for drug evaluation studies for the study of osteoarthritis.

EXAMPLE 5

Slowing the Development of Osteoarthritis by

Dehybromohymenialdisine (Z-DBHA) in the Hartley Guinea Pig

Model

Surgery was performed on twenty-four male Hartley guinea pigs during which the joint instability was induced according to the procedure described in Example 4.

The animals were divided into four groups of six. Beginning two weeks following surgery, each animal in the first two groups was given weekly intraarticular injections into the surgically treated joints of 0.3 mg (6 mg/ml) or 1.5 mg of Z-debromohymenialdisine (30 mg/ml) in a vehicle containing carboxymethylcellulose (2 mg/ml saline) and polysorbate 80 (0.5 mg/ml saline). Total volume of the injection was 50 μl. Group III animals were given weekly intraarticular injections of a placebo, while Group IV animals were left untreated. The treatments were continued for seven weeks.

Figure 4:
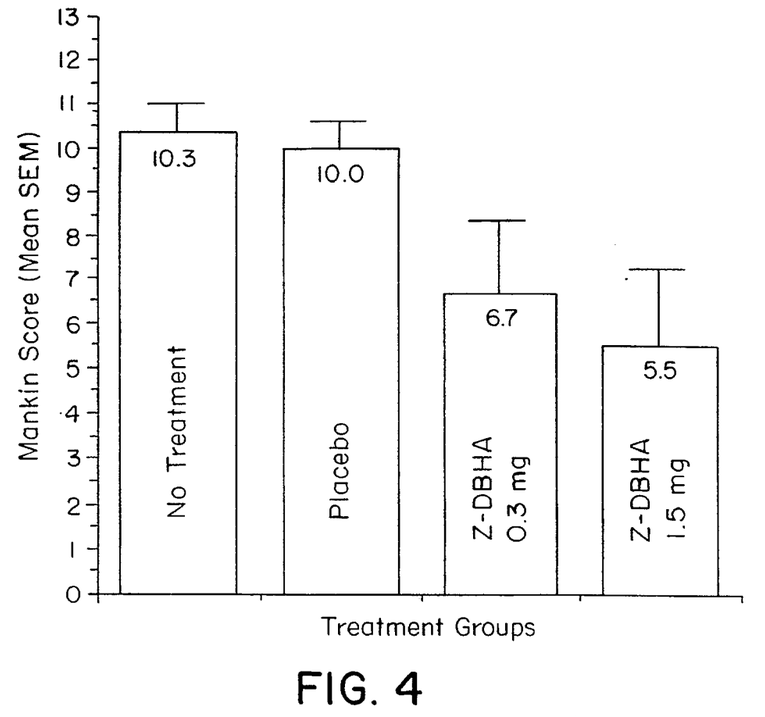
FIG. 4 is a graph illustrating the effect of Z-debromohymenialdise in slowing the development of osteoarthritis in the Hartley guinea pigs following surgical induction of joint instability.

At the termination of the system, the animals were euthanized and radiographic evaluation of the knees was performed as described in Example 5 using the Mankin criteria. The results of the histological evaluation at seven weeks post surgery are depicted in FIG. 4. Results for each of the Mankin criteria are given in the Table.

TABLE

|  | Structure | Cells | Safranin O | Tidemark |
|---|---|---|---|---|
| No Treatment | 4.6 | 1.6 | 2.3 | 4/6 |
| Z-DBHA 0.3 mg | 3.5 | 1.2 | 1.5 | 3/6 |
| Z-DBHA 1.5 mg | 1.6 | 1.5 | 1.1 | 1/6 |

Value given for Structure, Cells, and Safranin O are mean values.
Values for Tidemark Penetration are incidence figures.

The results indicate that there was a disease progression to a mean Mankin score of 10.3 for untreated animals and 10.0 for animals treated with the placebo. In contrast, animals treated with Z-debromohymenialdisine showed a significant reduction in disease progression. A dose of 0.3 mg/week resulted in disease progression to a mean Mankin score of 6.7, while a dose of 1.5 mg/week resulted in disease progression to a mean Mankin score of only 5.5. The results with 1.5 mg/week dose regimen, when compared to the No Treatment group by an unpaired t test gave a p value of 0.03 (significant) while the lower dose regiment of 0.3 mg/week gave a p value of 0.07 (marginally significant). When compared by non-parametric tests, which makes no assumption about the distribution of the data, the high dose (1.5 mg/week) was marginally significant (p=0.06) and the lower dose (0.3 mg/week) had a value compared to the No Treatment group of 0.130 (not significant).

In all cases every index of the Mankin scoring criteria has shown improvement when compared with the No Treatment Group. In all but the cellular evaluation the higher dose (1.5 mg/week) gave values that were consistent with a dose responsive relationship. Thus, Z-debromohymenialdisine was able to diminish the structural and biochemical changes as they are reflected by the loss of Safranin O staining in developing osteoarthritis.

These results demonstrate that Z-debromohymenialdisine is effective in slowing joint degeneration and cartilage degradation associated with osteoarthritis in animal models.

Equivalents

Those skilled in the art will know, or be able to ascertain using no more than routine experimentation, many equivalents to the specific embodiments of the invention described herein. These and all other equivalents are intended to be encompassed by the following claims.

We claim:

1. A method of treating an individual or animal with osteoarthritis, comprising administering to the individual a composition comprising a therapeutically effective amount of a compound having the following structure:

wherein R1 and R2 are each independently selected from the group consisting of -H and a halogen; and wherein X is selected from the group consisting of:

and physiologically active salts thereof.

2. The method of claim 1 wherein X is:

and physiologically active salts thereof.

3. The method of claim 2 wherein the halogen is -Br.

4. The method of claim 2 wherein R1 is H.

5. The method of claim 2 wherein R1 and R2 are -H.

6. The method of claim 5 wherein the composition is administered orally.

7. The method of claim 5 wherein the composition is administered topically.

8. The method of claim 5 wherein the composition is administered parenterally.

9. The method of claim 5 wherein the composition is administered intra-articularly.

10. The method of claim 5 wherein the composition additionally comprises a pharmacologically active agent.

11. The method of claim 10 wherein the pharmacologically active agent is selected from the group consisting of an analgesic, asteroid, a non-steroidal anti-inflammatory drug and a matrix metalloproteinase inhibitor.

12. The method of claim 5 wherein the composition additionally comprises a suitable pharmaceutical carrier.

* * * * *

UNITED STATES PATENT AND TRADEMARK OFFICE
CERTIFICATE OF CORRECTION

PATENT NO. : 5,591,740

DATED : January 7, 1997

INVENTOR(S) : Stewart Chipman and David John Faulkner

It is certified that error appears in the above-indentified patent and that said Letters Patent is hereby corrected as shown below:

In Column 14, line 18: After the word "and", in the lower right side of the forumula, before the comma, the "CH" should be deleted and a single bond should be inserted therefor. The correct formula would therefore be:

UNITED STATES PATENT AND TRADEMARK OFFICE
CERTIFICATE OF CORRECTION

PATENT NO. : 5,591,740

DATED : January 7, 1997

INVENTOR(S) : Stewart Chipman and David John Faulkner

It is certified that error appears in the above-identified patent and that said Letters Patent is hereby corrected as shown below:

In Column 14, line 52:  After the word "analgesic", delete the word "asteroid" and insert therefor --a steroid--.

Signed and Sealed this

Twenty-fifth Day of March, 1997

Attest:

BRUCE LEHMAN

Attesting Officer

Commissioner of Patents and Trademarks